United States Patent [19]

Jones

[11] Patent Number: 5,222,987
[45] Date of Patent: Jun. 29, 1993

[54] COMPOSITE MATERIAL FOR USE IN A PROSTHETIC DEVICE

[75] Inventor: Michael E. B. Jones, Chester, United Kingdom

[73] Assignee: Imperial Chemical Industries PLC, England

[21] Appl. No.: 506,242

[22] Filed: Apr. 9, 1990

[30] Foreign Application Priority Data

Apr. 12, 1989 [GB] United Kingdom ............... 8908215

[51] Int. Cl.⁵ .............................................. A61F 2/54
[52] U.S. Cl. .................................... 623/66; 623/16; 433/228.1; 428/290; 523/115
[58] Field of Search ............... 623/16, 66; 433/228.1; 428/290, 424.8; 522/14, 30, 36; 523/115, 116

[56] References Cited

U.S. PATENT DOCUMENTS

| | | | |
|---|---|---|---|
| 3,814,791 | 6/1974 | Jones | 264/164 |
| 4,089,762 | 5/1978 | Frodsham | 522/14 |
| 4,089,763 | 5/1978 | Dart et al. | 433/228.1 |
| 4,110,184 | 8/1978 | Dart et al. | 522/18 |
| 4,131,597 | 12/1978 | Bluethgen et al. | 260/42.18 |
| 4,235,686 | 11/1980 | Dart et al. | 522/14 |
| 4,403,607 | 9/1983 | Woo et al. | 623/16 |
| 4,411,625 | 10/1983 | Koblitz et al. | 523/115 |
| 4,602,076 | 7/1986 | Ratcliffe et al. | 522/13 |

FOREIGN PATENT DOCUMENTS

| | | |
|---|---|---|
| 0274203 | 7/1978 | European Pat. Off. |
| 0013491 | 7/1980 | European Pat. Off. |
| 0090493 | 10/1983 | European Pat. Off. |
| 112650 | 7/1984 | European Pat. Off. |
| 0162651 | 11/1985 | European Pat. Off. |
| 1465897 | 3/1977 | United Kingdom |
| 1494903 | 12/1977 | United Kingdom |

Primary Examiner—Randall L. Green
Assistant Examiner—Paul Prebilic
Attorney, Agent, or Firm—Cushman, Darby & Cushman

[57] ABSTRACT

A composite material in substantially two-dimensional or planar or sheet form, which material comprises:

(a) at least one layer of a fiber-like or fabric material; and (b) at least one layer of a composition which comprises a polymer, a curable resin and an addition-polymerizable initiator composition.

The composite material may be cured to form a prosthetic device, e.g. a rib cage.

20 Claims, 1 Drawing Sheet

FIGURE
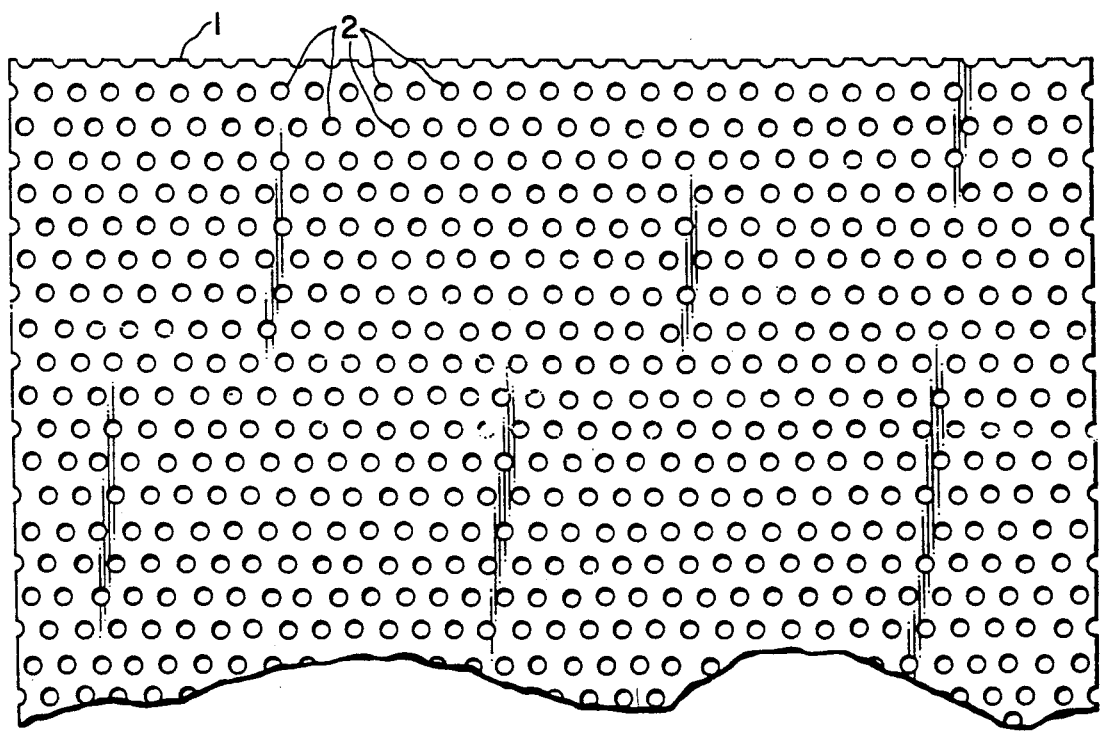

COMPOSITE MATERIAL FOR USE IN A PROSTHETIC DEVICE

The present invention relates to prosthetic devices, particularly for rib or thoracic cage replacement, and to composite materials useful in the preparation thereof.

Adequate reconstruction of chest wall defects has presented a difficult problem for many years. Employment of autogenous tissue in such reconstruction is highly desirable and methods for reconstructing small defects using autogeneous tissue, e.g. using periosteum and/or osseus flap techniques, are well known. Where there is a large chest wall defect, grafts, e.g. fascia lata or rectus sheath, may be adequate for closure of the defect but do not provide a thoracic wall reconstruction with long-term stability.

Metal, e.g. tantalum and stainless steel, prostheses in, for example, mesh form have been proposed for reconstructing chest walls. However, there is a tendency for undesirable fragmentation, and generation of metallic slivers, to occur.

Teflon (RTM) mesh has been used for reconstructing chest walls but in large defects it often requires additional support.

Lucite (RTM) plates have been proposed for reconstructing chest walls but require extensive pre-operative treatment, e.g. cutting, shaping and drilling of holes for sutures.

Sponges, e.g. Ivalon (RTM), and glass-fibre have been used for reconstructing chest walls but, where infection develops, have proved troublesome.

Recently, Marlex (RTM) mesh has been used in combination with conventional surgical methacrylate cement for reconstructing chest walls. and methacrylate surgical cement suffers from certain disadvantages and provides certain difficulties. For example, it requires assembly/manipulation in the operating theatre, e.g. the cement has to be worked into one or more Marlex meshes; it has limited working life, liquid methyl methacrylate containing an addition-polymerisation accelerator is mixed with polymethyl methacrylate powder containing addition-polymerisation initiator: it exudes an unpleasant smell which often irritates both patient and operating-theatre staff: it tends to have a tacky surface; and the mechanical properties of the prosthetic product produced therefrom tend to be irreproducible.

SUMMARY OF THE INVENTION

We have now devised a composite material which can be used in the preparation of a prosthetic device and which overcomes many of the above disadvantages and difficulties.

The composite material has the further advantage that (i) there is no liquid monomer which can readily extrude therefrom to irritate, aggravate or endanger the life of the patient; (ii) it is substantially non-sticky and non-tacky; (iii) it saves valuable time before the wound is closed; and (iv) it can easily be shaped/formed to correspond to the chest wall cavity and subsequently caused to harden.

According to a first aspect of the present invention there is provided a composite material in substantially two-dimensional or planar or sheet form, useful in the preparation of a prosthesis which composite material comprises
(a) at least one layer of a fibrous or fabric material; and
(b) at least one layer of a composition which comprises an oligomer or polymer, a curable resin, and an addition-polymerisable initiator composition.

The composite material of the present invention may be cured by the application thereto in situ on the patient of suitable radiation, e.g. infra-red, ultra-violet, ultrasonic or preferably visible light. However, we do not exclude the possibility that it may be cured by the exposure to air or moisture.

By "visible light" we mean light having a wavelength in the range of 400 to 750 nm.

According to a preferred aspect of the present invention there is provided a composite material in substantially two-dimensional or planar or sheet form, useful in the preparation of a prosthesis which material comprises
(a) at least one layer of a fibrous or fabric material; and
(b) at least one layer of a composition which comprises a polymer, a curable resin and a photo-initiator composition, as hereinafter described.

According to a second aspect of the present invention there is provided a prosthetic product preparable by photo-curing the composite material of the preferred aspect of the present invention.

According to a third aspect of the present invention there is provided a prosthetic product comprising a plurality of superimposed layers each of which comprises a photo-cured composition interwoven by one or more layers of a fibrous or fabric material.

According to a fourth aspect of the present invention there is provided a method for reconstructing a chest wall which method comprises at least the steps of covering a void in the chest wall with a composite material of the preferred aspect of the present invention and subjecting it to suitable radiation to cure the curable resin therein.

DETAILED DESCRIPTION OF THE INVENTION

The fibrous or fabric material preferably provides between 0.1 and 20 w/w % of the prosthetic device of the present invention more preferably about 3 w/w %. However, we do not exclude the possibility that a weight % outside the aforementioned range may be used.

In the composite material according to the present invention the composition typically comprises from 5%–95% by weight of the polymer and 95%–5% by weight of the curable resin, preferably 5–60% of the polymer and 95–40% by weight of the curable resin.

The composite material according to the first aspect of the present invention is self-supporting but can be readily worked by the skilled man to give a desired shape which is made permanent by curing.

The composite material according to the present invention may be distorted to afford a 3-dimensional object and retain that shape, i.e. it has sufficient inherent strength to deshape it (i.e. return) to its original, e.g. planar, form before it is cured.

The thickness of the composite material according to the present invention is typically between 0.5 and 5 mm, preferably between 2 and 4 mm. It will be appreciated that the thickness will be chosen in the light of inter alia the size and shape of the reconstruction and the physical condition, e.g. age or weight, of the patient to whom it will be applied.

The composite material according to the present invention may be readily cut to a desired size and shaped by a surgical professional in theatre. Sutures may lie close to the edge of the prosthesis and because of the presence of the fibre-like material do not "pull-through". The prosthetic is typically attached to the rib cage at points conventionally used for attaching protheses, e.g. periosteum.

Preferably the substantially planar composite material (1) according to the present invention is provided with a plurality of small ports (2) throughout the entire area thereof; each port extending from one face to the other face. The number of ports per unit area and the size thereof may be readily determined by the skilled man. It will be appreciated that where the composite material is cut to an appropriate shape and size it may be cut such that at least some of the ports are provided adjacent the periphery. Such peripheral ports facilitate the suturing of the device to the human body. Preferably suturing occurs after the curing step.

BRIEF DESCRIPTION OF THE DRAWING

The accompanying drawing is a fragmental perspective view illustrating the invention.

The composite material according to the present invention is pliable, flexible at body temperature. It is believed that plasticisation of the polymer therein by the curable resin contributes to such pliability, etc.

The prosthetic product according to the present invention comprises orientated reinforcement formed of a continuous biocompatible fibrous material that is embedded in the cured composition. Preferably the fibrous material extends throughout the entire area of the prosthetic device. It may be non-woven, woven or preferably knitted, provided that it allows the composite material to be readily shapeable by hand to correspond to the contour of the chest wall in the proximity of the cavity to be covered.

The fabric reinforcement may provide a layer at one or both surfaces, or intermediate the surfaces, of the prosthesis. Where it provides one layer only this may lie on the superficial or deep aspect of the composite. The number of layers of fabric in the composite material may be readily chosen by the skilled man to afford a prothetic device having the desired mechanical properties.

The fibrous or fabric material is typically synthetic, for example polyester (e.g., Terylene (RTM)), polyamide (e.g. nylon), poly-acrylic (e.g. Orlon (RTM)), polyurethane, or preferably high density polyethylene (e.g. Marlex (RTM) ex C R Bard Inc.). We do not exclude the possibility that a natural fibre, e.g. wool or cotton, or fibres from a biodegradable polymer, e.g. polyhydroxy butyrate, may be used but this is not preferred.

The curable resin of which the composite material according to the present invention is comprised bears on average more than one addition—polymerisable olefinically unsaturated carbon-carbon double bond per molecule. It is often preferred that it comprises a plurality of such carbon-carbon double bonds. The curable resin, which may be neat or an admixture, will be chosen in the light of (i) the processability properties required in the composite material and (ii) the properties of the prosthetic device prepared therefrom. Preferably the resin comprises one or more addition-polymerisable oligomers.

As examples of such addition-polymerisable oligomers may be mentioned inter alia: vinyl urethanes, the di-methacrylate of oxyethlated bis-phenol A, e.g. Diacryl 101 (RTM), or perferably an oligomer derived from an aromatic compound and an aldehyde and bearing pendant and/or terminal addition polymerisable substituents (hereinafter referred to for convenience as "aromatic oligomer"), or more preferably, such an oligomer derived from diphenyl ether, formaldehyde and methacrylic acid. Such diphenyl ether-derived oligomers are more fully described in our EP 0,112,650, the disclosure in which is incorporated herein by way of reference.

The composition of which the composite material according to the present invention is comprised may comprise, in addition to the addition-polymerisable oligomer, a low viscosity, reactive diluent of low volatility. As examples of such diluents may be mentioned non-toxic monomers

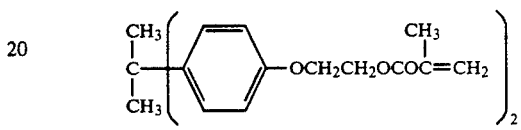

or preferably triethyleneglycol dimethacrylate.

The presence of such a diluent in the composition often reduces the viscosity thereof. This reduction in viscosity often facilitates the preparation of the composite material by the process hereinafter described and allows certain properties, e.g. water-uptake, of the prosthetic device prepared therefrom to be adjusted. It will be appreciated that where the aforementioned diluent is a monomer containing one carbon-carbon double bond it reduces the cross-link density of the composite. Where a rective diluent is present in the composition the nature and concentation thereof may be determined by the skilled man by simple experiment.

As examples of polymers which may be present in the composition of which the composite material according to the present invention is comprised may be mentioned inter alia cured epoxide resins (curable at low, e.g. room, temperature), or preferably a polyurethane, more preferably a polyurethane derived from an aliphatic isocyanate, e.g. hexamethylene diisocyanate, and an aliphatic primary diol. One or more polymers may be present in the composition.

It is preferred that the polymer and the cured resin are compatible, i.e. homogeneity is maintained during the curing step of the composite material according to the present invention such that visible phase separation does not occur and when examined in section by optical microscopy the cured composite material in the prosthetic device according to the present invention appears to be homogeneous. For example, where the polymer is a polyurethane and the curable resin comprises an aromatic oligomer as hereinbefore-defined the polyurethane regions are often so small that they cannot be resolved and the polymer domains are not apparently discrete. This facilitates the speed and depth of cure. It is preferred that there is a degree of chemical bonding between the polymer and the cured resin which tends to prevent phase separation.

Preferably the composition which provides at least one layer of the composite material of the present invention is prepared by impregnating the fibres or fabric with an appropriate liquid, preferably of low viscosity, and then allowing or causing the liquid to harden. An integral composite material is obtained. Preferably the appropriate liquid is prepared by mixing, e.g. dispersing or dissolving, precursors of the polymer in the curable resin, which polymers are then allowed or caused to interact to prepare the polymer. In an alternative method of preparing such a liquid, high polymer is dissolved in liquid resin, often at high temperature, the fibres or fabric are impregnated therewith and the solution is allowed or caused to cool. However, this alternative method includes treatment of a high viscosity liquid and/or a high temperature and is not preferred.

Where the polymer is a polyurethane the composition is typically prepared by mixing the curable resin, e.g. the aforementioned aromatic oligomer, with the precursors of the polyurethane, charging a suitable mould with the mixture and then effecting polymerisation of the aforementioned precursors.

Preferably gelation of the aforementioned precursors to form the polyurethane, where the polymer is a polyurethane, is effected at about or below ambient temperature, e.g. at or below 30° C.

Where a mould is used in the preparation of the composite material it is typically made of a metal, e.g. aluminium, or an alternative material resistant to the casting conditions, of a suitable shape and depth, e.g. 25 cm×25cm×0.3 cm, the fibrous material is often incorporated into the intimate mixture prior to preparation of the polymer. For example, in a first procedure: the fibrous material may lie on the bottom of the mould and the mixture poured onto it; in a second procedure: a layer of fibrous material is disposed on the top of the mixture (which may contain a layer from the first procedure such that a first sandwich structure is prepared); in a third procedure: a layer of fibrous material is disposed on a layer of mixture in the mould and then a further layer of the mixture is prepared. Preparation of the polymer is then allowed or caused to proceed and when the polymer has been prepared the composite material may be demoulded.

Where a mould is used it is preferably provided with a plurality of projections of a suitable height and cross-section which may be disposed regularly or randomly and around which the resin and pre-cursors flow. The precursors are polymerised in the mould and ports corresponding to the aforementioned projections are generated in the substantially planar composite material; which ports facilitate suturing as hereinbefore described.

In an alternative method of preparation, the aforementiond ports can be punched in the sheet of composite material of the present invention when it has gelled.

It will be appreciated that in the preparation of a composite material according to the preferred aspect of the present invention, wherein the composite material comprises a photo-initiator composition, the aforementioned impregnation will be carried out in light to which the photo-initiator is not sensitive.

It is often preferred that the refractive indices of the composition and the fibre are substantially the same such that the composite material of the present invention appears homogeneous to the human eye prior to the curing thereof, particularly in the preferred aspect of the present invention.

The fibre and the resin are chosen such that there is an affinity between them in the uncured and cured states such that in the cured state the resin adheres to the fibres to prevent the ingress of water which could cause the prostheses to deteriorate.

We do not exclude the possibility that the composite material of the present invention may contain a particulate filler, e.g. hydroxy apatite, but this is not preferred. Where particles are present they should preferably have a refractive index equal to that of the composition such that in the preferred aspect of the present invention they do not reduce the transparency/translucency of the composite and impede unduly the curing of the resin.

The photo-initiator compositions for use in the preferred aspect of the present invention generates free-radicals on exposure to a source of electromagnetic radiation which act as an initiator for the curing of the curable resin. It may consist of a single compound or it may comprise at least two components. Typically, it comprises any of the known photo-initiator systems which are used to initiate addition-polymerisation of polymerisable olefinically unsaturated monomers. As examples of such compositions may be mentioned inter alia (a) mixtures of Michler's ketone and benzil or preferably benzophenone, typically in a weight ratio of about 1:4; (b) the coumarin-based photo-initiator systems described in U.S. Pat. No. 4,289,844, (c) combinations of hexaarylbisimidazoles and leuco dyes, (d) cyclohexadiene-leuco dye systems described in U.S. Pat. No. 4,241,869, (e) systems based on dimethyoxyphenyl-acetophenone (benzil dimethyl ketal) and/or diethoxyacetophenone or (f) preferably mixtures of amines and ketones as disclosed in our UK patent specifications Nos. 1,408,265 and 1,494,903, e.g. camphorquinone, fluorenone or morpholine and N,N-dimethylamino-ethyl methacrylate, typically in a weight ratio of about 1:1. It is often preferred that the photo-initiator composition further comprises a peroxide compound, e.g. a peroxybenzoate, which improves the rate and/or depth of cure of the composite material.

Where the preferred mixture of amine and ketone is used the ketone may, for example, be present in the composite material in a concentration in the range 0.01% to 2% by weight of the curable resin in the composite material although concentrations outside this range may be used if desired. Preferably the α-diketone is present in a concentration of 0.2% to 1.5% by weight of the curable resin in the composite material. is used the amine is an organic amine having the formula $R^1_3N$ where the groups $R^1$, which may be the same or different, are hydrogen atoms, hydrocarbyl groups, substituted hydrocarbyl groups or groups in which two units $R^1$ together with the nitrogen atom from a cyclic ring system; no more than two of the units $R^1$ being hydrogen atoms and where N is attached directly to an aromatic group $R^1$, at least one of the other units $R^1$ has a

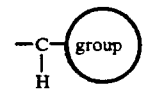

attached to the nitrogen atom.

The amine is preferably present in the composite material in concentration in the range 0.01% to 2% by weight of the polymerisable material in the composition although concentrations outside this range may be used if desired.

The photo-initiator composition used in the preferred aspect of the present invention is preferably chosen such that it is activated by the in-situ light in the operating theatre which typically has a spectral distribution with a maximum at about 470 nm. A preferred example of a photo-initiator system which is activatable by light of such a wavelength comprises camphor quinone and N,N-dimethylaminoethyl methacrylate.

However, we do not exclude the possibility that a discrete light source may be employed specifically to activate the photo-initiator system.

Whereas we do not exclude the possibility that UV radiation may be used to cure the curable resin this is not preferred.

The time required to produce a prosthetic device according to the second aspect of the present invention will depend inter alia on the intensity of the visible light used, the nature and concentration of the photo-sensitive catalyst and the nature of the curable resin.

As the composite material according to the preferred aspect of the present invention is sensitive to and curable on exposure to visible light, it is preferably stored between layers of an opaque film-like material, e.g. polythene, in a substantially light-tight container. The composite material of the present invention can be used to reconstruct ribs having a hole of a few tens of square centimeters, e.g. 15×15 cms, from which a few, e.g. 4, ribs have been removed. It can be used after full thickness chest wall resection and immediate reconstruction. Thus reconstruction can advantageously be performed in a single operation.

The prosthesis of the present invention often becomes incorporated into the living tissue, adds stability to the thoracic wall, does not interfere with physiological chest wall movement, is physiochemically inert and does not potentate infection.

The prosthesis is typically used externally, i.e. extraplurally situated on the outside, of the chest wall and sutured thereto.

The skilled man will perform those pre-operative procedures to evaluate the possibility of using the prosthesis of the present invention.

Furthermore, the skilled man will use those post-operative procedures which he considers appropriate, e.g. for cosmetic results. For example, he may use certain flaps, e.g. latissimus dorsi myocutaneous flap.

It will be appreciated that the prosthesis of the present invention should be transparent to x-rays to facilitate the examination of under-lying tissue.

Whereas the present invention has been described hereinbefore with particular reference to the rib cage, the skilled man will appreciate that certain aspects therefore are applicable to certain further portions of the human body, e.g. a cranial plate for the cranium. He will be able to determine the properties needed in a device for use in such further portions by simple experimentation.

It will be appreciated that the composite material of the present invention which are to be used as internal prosthetic devices are preferably packaged in a suitable container, e.g. a plastic bag, and sterilised as part of the manufacturing process. Such sterilisation, where it is carried out, may be effected by radiation, heat treatment or chemical means, provided that it does initiate the curing of the curable resin, or degrade the polymer or fibre material.

It will be appreciated that the skilled man may test the suitability of the prosthetic device for use in any particular location by appropriate tests known in the art.

The present invention is further illustrated by reference to the following Examples.

In the Examples all "parts" are by "weight".

EXAMPLE 1

This Example illustrates a composite material according to the present invention.

Polyurethane precursors, i.e. 4,4-(dihydroxyethyl)-diphenyl-2,2-propane (7.3 parts), tri-methylol-propane (7.8 parts) and hexamethylene diisocyanate (19.5 parts), were added to a stirring mixture at 40° C. of triethylene glycol di-methacrylate (31.5 parts) and an oligomer (31.5 parts) obtained by the procedure described in Example 14 of our EP 0,112,650 (having M=760 and functionality=2.6). A mobile transport solution was obtained (Solution A).

The photo-initiator system, i.e. camphor quinone (0.8 parts) and N,N-dimethylaminoethyl methacrylate (0.5 parts), a polyurethane catalyst, i.e. di-butyl tin dilaurate (0.1 parts); and tert-butyl peroxybenzoate (1.0 parts), were added to Solution A. The mixture was stirred for 5 minutes and then subjected to a vacuum of 25 mm Hg for 2 minutes. A mobile pale yellow solution was obtained (Solution B).

A portion of Solution B was poured into, to fill, an aluminum mould (10 cm×10 cm×0.3 cm) in which was disposed a sheet of Marlex (RTM) fabric under light tension across the centre of the mould. The filled mould was transferred to a level, darkened area and kept at 45° overnight while the polyurethane was prepared.

The product from this treatment was a transparent, soft, flexible composite sheet which had a tack-free surface and in which the fibrous reinforcement was continuous and disposed intermediate the two faces of the sheet. It was readily cut with scissors or scalpel and was easily shaped under light manual pressure.

EXAMPLE 2

This example illustrates a prosthetic device according to the present invention.

A sample was cut from the composite sheet prepared in Example 1 and illuminated at the focus of a Hanalux (RTM) operating-theatre light for 60 seconds. The sample hardened and could not easily be deformed or re-shaped by manual pressure. The room temperature flexural properties of the hardened sample were determined and are shown in Table 1.

In a comparative test, a composite was prepared from a commercially available bone-cement and two layers of Marlex. In order to obtain material suitable for testing it was necessary to adopt fabrication conditions, i.e. compression moulding, which gave a uniform product. It will be appreciated that such conditions are not available to the surgeon in theatre and therefore the results recorded for the comparative test are significantly better than those which could be obtained from a sample of commercially available material prepared manually in theatre.

TABLE 1

| Example No | Flexural Strength M.Pa | Flexural Modulus G.Pa |
|---|---|---|
| 2 | 127.5 | 2.32 |
| CT | 66.2 | 2.93 |

CT: Comparative test

From Table 1 it can be seen that the prosthetic device according to the present invention is significantly stronger than a conventional bone-cement based prosthetic device (even when the latter was prepared under optimal laboratory conditions).

EXAMPLE 3

This Example illustrates the use of a prosthetic device according to the present invention.

A sample of flexible composite sheet material measuring 9.5×9.0×0.28 cms was prepared as described in Example 1.

A series of 0.1 cm diameter holes were cut around the periphery of the sample (using a leather punch) at about 1 cm intervals. This sample was then used to repair an opening, which had been surgically created in the chest-wall of an adult pig. The holed sample was cut and moulded to the required anatomical shape; it was held under the theatre lights for about 60 seconds to effect hardening (cure). The prosthetic device was then sutured into place using the punched holes adjacent to the periphery thereof.

After six months in vivo the prosthetic device was removed and examined visually, microscopically and mechanically. The prosthetic device had become slightly opaque but no physical deterioration could be detected at the margins, surfaces or in the bulk of the material, it remained strong and tough when flexed manually.

Rectangler test pieces were cut from this sample and were found to have an average flexural modulus of 2.10 G.P.a and a flexural strength of 123.2 M.P.a confirming that little deterioration had occurred during this period of implantation.

I claim:

1. A composite material in substantially planar sheet form, useful in the preparation of a prosthesis, which material comprises:
   (a) at least one layer of a fibre or fabric; and
   (b) at least one layer of a composition which comprises a polymer, a curable resin and an addition-polymerisable photo-initiator composition;
wherein the fibre or fabric comprises high density polyethylene.

2. A composite material as claimed in claim 1 wherein the photo-initiator is activatable by electromagnetic radiation of wavelength 400 to 750 nm.

3. A composite material as claimed in claim 1 provided with a plurality of small ports.

4. A composite material as claimed in claim 1 wherein the polymer comprises a polyurethane.

5. A composite material as claimed in claim 1 wherein the curable resin comprises an addition-polymerisable oligomer.

6. A composite material as claimed in claim 5 wherein the oligomer comprises an aromatic oligomer.

7. A composite material as claimed in claim 5 wherein the curable resin further comprises a low viscosity addition-polymerisable reactive diluent.

8. A composite material as claimed in claim 2 wherein the photo-initiator composition comprises an alpha-diketone and an amine.

9. A prosthetic device comprising a plurality of superimposed layers of each of which comprises a material comprising:
   (a) at least one layer of a fibre or fabric; and
   (b) at least one layer of a composition which comprises a polymer, a curable resin and an addition-polymerisable photo-initiator composition;
wherein the fibre or fabric comprises high density polyethylene.

10. A prosthetic device as claimed in claim 9 wherein the polymer and the cured resin are compatible.

11. A composite material in substantially planar or sheet form, useful in the preparation of a prosthesis, which material comprises:
   (a) at least one layer of a fibre or fabric; and
   (b) at least one layer of a composition which comprises a polymer, a curable resin and an addition-polymerisable photo-initiator composition;
wherein the fibre or fabric and the composition have substantially the same reflective indices.

12. A composite material as claimed in claim 11, wherein the photo-initiator is activatable by electromagnetic radiation of wavelength 400 to 750 nm.

13. A composite material as claimed in claim 11 provided with a plurality of small ports.

14. A composite material as claimed in claim 11, wherein the polymer comprises a polyurethane.

15. A composite material as claimed in claim 11, wherein the curable resin comprises an addition-polymerisable oligomer.

16. A composite material as claimed in claim 11, wherein the oligomer comprises an aromatic oligomer.

17. A composite material as claimed in claim 11, wherein the curable resin further comprises a low viscosity addition-polymerisable reactive diluent.

18. A composite material as claimed in claim 11, wherein the photo-initiator composition comprises an alpha-diketone and an amine.

19. A prosthetic device comprising a plurality of superimposed layers each of which comprises a material comprising:
   (a) at least one layer of a fibre or fabric; and
   (b) at least one layer of a composition which comprises a polymer, a curable resin and an addition-polymerisable photo-initiator composition;
wherein the fibre or fabric and the composition have substantially the same refractive indices.

20. A prosthetic device as claimed in claim 19, wherein the polymer and the cured resin are compatible.

* * * * *